(12) United States Patent
Carnes et al.

(10) Patent No.: US 7,596,891 B2
(45) Date of Patent: Oct. 6, 2009

(54) SHOE HOUSING

(75) Inventors: James Carnes, Portland, OR (US); Scott Tomlinson, Portland, OR (US); Stephen Michael Vincent, Portland, OR (US)

(73) Assignee: adidas International Marketing B.V., Amsterdam (NL)

( * ) Notice: Subject to any disclaimer, the term of this patent is extended or adjusted under 35 U.S.C. 154(b) by 457 days.

(21) Appl. No.: 11/394,132

(22) Filed: Mar. 30, 2006

(65) Prior Publication Data
US 2006/0283050 A1 Dec. 21, 2006

(30) Foreign Application Priority Data
Mar. 31, 2005 (DE) .................. 10 2005 014 709

(51) Int. Cl.
A43B 5/00 (2006.01)
A43B 13/18 (2006.01)
(52) U.S. Cl. ............................ 36/132; 36/25 R; 36/136
(58) Field of Classification Search .................... 36/132, 36/25 R, 136
See application file for complete search history.

(56) References Cited

U.S. PATENT DOCUMENTS

| | | | |
|---|---|---|---|
| 1,597,823 A | 8/1926 | Randolph | |
| 2,760,278 A | 8/1956 | Agrillo | |
| 2,897,609 A | 8/1959 | Bodkin | |
| 4,175,446 A | 11/1979 | Crowninshield et al. | |
| 4,402,147 A | 9/1983 | Wu | |
| 4,649,552 A | 3/1987 | Yukawa | |
| 4,703,445 A * | 10/1987 | Dassler ........................ | 702/160 |
| 4,771,394 A | 9/1988 | Cavanagh | |
| 4,814,661 A | 3/1989 | Ratzlaff et al. | |
| 4,870,700 A | 9/1989 | Ormanns et al. | |
| 5,086,574 A | 2/1992 | Bacchiocchi et al. | |
| 5,179,792 A | 1/1993 | Brantingham | |
| 5,269,081 A | 12/1993 | Gray | |
| 5,285,586 A | 2/1994 | Goldston et al. | |
| 5,325,869 A | 7/1994 | Stokes | |
| 5,335,188 A | 8/1994 | Brisson | |
| 5,357,696 A | 10/1994 | Gray et al. | |
| 5,369,896 A | 12/1994 | Frachey et al. | |

(Continued)

FOREIGN PATENT DOCUMENTS

DE  1 013 126  8/1957

(Continued)

OTHER PUBLICATIONS

Article, "adidas and Polar Introduce the World's First Completely Integrated Training System", www.adidas-Polar.com, Aug. 4, 2005, 2 pages.

(Continued)

*Primary Examiner*—Ted Kavanaugh
(74) *Attorney, Agent, or Firm*—Goodwin Procter LLP

(57) ABSTRACT

The invention relates to a shoe with a sole unit, where the sole unit includes a recess for removably receiving a housing of an electronic assembly, for example, an electronic pedometer, an accelerometer, or a speed sensor. Further, the invention relates to a housing for receiving an electronic assembly, for example, a pedometer, an accelerometer, or a speed sensor, where the housing has an outer shape corresponding to the shape of a recess formed in a shoe sole.

21 Claims, 5 Drawing Sheets

U.S. PATENT DOCUMENTS

| | | |
|---|---|---|
| 5,373,651 A | 12/1994 | Wood |
| 5,383,290 A | 1/1995 | Grim |
| 5,471,405 A | 11/1995 | Marsh |
| 5,473,518 A | 12/1995 | Haber et al. |
| 5,490,338 A | 2/1996 | Hwang et al. |
| 5,500,635 A | 3/1996 | Mott et al. |
| 5,557,259 A | 9/1996 | Musa |
| 5,557,865 A | 9/1996 | Sjosvard |
| 5,566,479 A | 10/1996 | Gray et al. |
| 5,574,432 A | 11/1996 | McCarthy |
| 5,583,776 A | 12/1996 | Levi et al. |
| 5,592,759 A | 1/1997 | Cox |
| 5,596,652 A | 1/1997 | Piatek et al. |
| 5,598,849 A | 2/1997 | Browne et al. |
| 5,636,146 A | 6/1997 | Flentov et al. |
| 5,640,786 A | 6/1997 | Buyayez |
| 5,644,858 A | 7/1997 | Bemis |
| 5,655,316 A | 8/1997 | Huang |
| 5,720,200 A | 2/1998 | Anderson et al. |
| 5,724,265 A | 3/1998 | Hutchings |
| 5,724,667 A | 3/1998 | Furuno et al. |
| 5,732,486 A | 3/1998 | Rapisarda |
| 5,748,087 A | 5/1998 | Ingargiola et al. |
| 5,775,005 A | 7/1998 | McClelland |
| 5,793,882 A | 8/1998 | Piatek et al. |
| 5,794,361 A | 8/1998 | Sadler |
| 5,813,142 A | 9/1998 | Demon |
| 5,875,571 A | 3/1999 | Huang |
| 5,890,997 A | 4/1999 | Roth |
| 5,918,502 A | 7/1999 | Bishop |
| 5,929,332 A | 7/1999 | Brown |
| 5,931,763 A | 8/1999 | Alessandri et al. |
| 5,937,462 A | 8/1999 | Huang |
| 5,955,667 A | 9/1999 | Fyfe et al. |
| 5,960,380 A | 9/1999 | Flentov et al. |
| 5,970,631 A | 10/1999 | Inman |
| 5,983,529 A | 11/1999 | Serna |
| 6,012,822 A | 1/2000 | Robinson |
| 6,013,007 A | 1/2000 | Root et al. |
| 6,014,080 A | 1/2000 | Layson, Jr. |
| 6,017,128 A | 1/2000 | Goldston et al. |
| 6,018,705 A | 1/2000 | Gaudet et al. |
| 6,052,654 A | 4/2000 | Gaudet et al. |
| 6,077,193 A | 6/2000 | Buhler et al. |
| 6,122,340 A | 9/2000 | Darley et al. |
| 6,122,846 A | 9/2000 | Gray et al. |
| 6,160,254 A | 12/2000 | Zimmerman et al. |
| 6,183,425 B1 | 2/2001 | Whalen et al. |
| 6,195,921 B1 | 3/2001 | Truong |
| 6,230,501 B1 | 5/2001 | Bailey, Sr. et al. |
| 6,266,623 B1 | 7/2001 | Vock et al. |
| 6,278,378 B1 | 8/2001 | Feiner et al. |
| 6,298,314 B1 | 10/2001 | Blackadar et al. |
| 6,312,361 B1 | 11/2001 | Hayes |
| 6,336,365 B1 | 1/2002 | Blackadar et al. |
| 6,357,147 B1 | 3/2002 | Darley et al. |
| 6,375,612 B1 | 4/2002 | Guichon et al. |
| 6,396,413 B2 | 5/2002 | Hines et al. |
| 6,424,264 B1 | 7/2002 | Giraldin et al. |
| 6,430,843 B1 | 8/2002 | Potter et al. |
| 6,493,652 B1 | 12/2002 | Ohlenbusch et al. |
| 6,496,787 B1 | 12/2002 | Flentov et al. |
| 6,498,994 B2 | 12/2002 | Vock et al. |
| 6,499,000 B2 | 12/2002 | Flentov et al. |
| 6,516,284 B2 | 2/2003 | Flentov et al. |
| 6,526,158 B1 | 2/2003 | Goldberg |
| 6,531,963 B1 | 3/2003 | Nyfelt |
| 6,536,139 B2 | 3/2003 | Darley et al. |
| 6,539,336 B1 | 3/2003 | Vock et al. |
| 6,560,903 B1 | 5/2003 | Darley |
| 6,569,092 B1 | 5/2003 | Guichon et al. |
| 6,589,630 B1 | 7/2003 | Crow |
| 6,600,407 B2 | 7/2003 | Paek et al. |
| 6,611,789 B1 | 8/2003 | Darley |
| 6,614,392 B2 | 9/2003 | Howard |
| 6,661,782 B1 | 12/2003 | Mustajarvi et al. |
| 6,788,200 B1 | 9/2004 | Jamel et al. |
| 6,807,753 B2 | 10/2004 | Steszyn et al. |
| 6,807,869 B2 | 10/2004 | Farringdon et al. |
| 6,808,462 B2 | 10/2004 | Snyder et al. |
| 6,813,586 B1 | 11/2004 | Vock et al. |
| 6,825,777 B2 | 11/2004 | Vock et al. |
| 6,856,934 B2 | 2/2005 | Vock et al. |
| 6,865,825 B2 | 3/2005 | Bailey, Sr. et al. |
| 6,876,947 B1 | 4/2005 | Darley et al. |
| 6,882,955 B1 | 4/2005 | Ohlenbusch et al. |
| 6,885,971 B2 | 4/2005 | Vock et al. |
| 6,898,550 B1 | 5/2005 | Blackadar et al. |
| 6,959,259 B2 | 10/2005 | Vock et al. |
| 6,963,818 B2 | 11/2005 | Flentov et al. |
| 7,062,225 B2 | 6/2006 | White |
| 7,072,789 B2 | 7/2006 | Vock et al. |
| 7,083,296 B2 | 8/2006 | Chiang et al. |
| 7,092,846 B2 | 8/2006 | Vock et al. |
| 7,107,706 B1 | 9/2006 | Bailey, Sr. et al. |
| 7,158,912 B2 | 1/2007 | Vock et al. |
| 7,162,392 B2 | 1/2007 | Vock et al. |
| 7,200,517 B2 | 4/2007 | Darley et al. |
| 7,204,041 B1 | 4/2007 | Bailey, Sr. et al. |
| 7,219,449 B1 | 5/2007 | Hoffberg et al. |
| 7,225,565 B2 | 6/2007 | DiBenedetto et al. |
| 2001/0054014 A1 | 12/2001 | Noda et al. |
| 2002/0022551 A1 | 2/2002 | Watterson et al. |
| 2002/0077883 A1 | 6/2002 | Lancos et al. |
| 2002/0080198 A1 | 6/2002 | Giraldin et al. |
| 2002/0091796 A1 | 7/2002 | Higginson et al. |
| 2002/0116147 A1 | 8/2002 | Vock et al. |
| 2002/0142887 A1 | 10/2002 | O'Malley |
| 2002/0147629 A1 | 10/2002 | Alsafadi et al. |
| 2002/0147642 A1 | 10/2002 | Avallone et al. |
| 2002/0152645 A1 | 10/2002 | Darley et al. |
| 2002/0156677 A1 | 10/2002 | Peters et al. |
| 2002/0165758 A1 | 11/2002 | Hind et al. |
| 2002/0173407 A1 | 11/2002 | Bowman |
| 2002/0174025 A1 | 11/2002 | Hind et al. |
| 2003/0009308 A1 | 1/2003 | Kirtley |
| 2003/0009382 A1 | 1/2003 | D'Arbeloff et al. |
| 2003/0009913 A1 | 1/2003 | Potter et al. |
| 2003/0040922 A1 | 2/2003 | Bodin |
| 2003/0056401 A1 | 3/2003 | Kwon |
| 2003/0090386 A1 | 5/2003 | Giraldin et al. |
| 2003/0097878 A1 | 5/2003 | Farringdon et al. |
| 2003/0120353 A1 | 6/2003 | Christensen |
| 2003/0160732 A1 | 8/2003 | Van Heerden et al. |
| 2003/0163287 A1 | 8/2003 | Vock et al. |
| 2004/0046692 A1 | 3/2004 | Robson et al. |
| 2004/0064974 A1 | 4/2004 | Schuster |
| 2004/0177531 A1 | 9/2004 | DiBenedetto et al. |
| 2004/0216330 A1 | 11/2004 | Swigart |
| 2005/0080566 A1 | 4/2005 | Vock et al. |
| 2005/0183292 A1* | 8/2005 | DiBenedetto et al. ......... 36/132 |
| 2006/0014645 A1 | 1/2006 | Yavitz |
| 2006/0020421 A1 | 1/2006 | Darley et al. |
| 2006/0031039 A1 | 2/2006 | Flentov et al. |
| 2006/0052983 A1 | 3/2006 | Vock et al. |
| 2006/0136173 A1 | 6/2006 | Case et al. |
| 2006/0156581 A1 | 7/2006 | Holden et al. |
| 2006/0235642 A1 | 10/2006 | Vock et al. |
| 2007/0006489 A1 | 1/2007 | Case et al. |
| 2007/0033838 A1 | 2/2007 | Luce et al. |

FOREIGN PATENT DOCUMENTS

| | | |
|---|---|---|
| DE | 34 47 171 | 9/1985 |

| | | |
|---|---|---|
| DE | 35 06 055 | 8/1986 |
| DE | 297 01 308 | 5/1997 |
| DE | 10201134 | 7/2003 |
| DE | 203 17 143 | 5/2004 |
| DE | 102005014709 | 10/2006 |
| EP | 0152057 | 8/1985 |
| EP | 0472110 | 2/1992 |
| EP | 1120056 | 8/2001 |
| EP | 1134555 | 9/2001 |
| EP | 1362522 | 11/2003 |
| EP | 1457128 | 9/2004 |
| FR | 2 743 701 | 7/1997 |
| JP | 60/084689 | 5/1995 |
| JP | 60-200120 | 10/1995 |
| JP | 2001-143049 | 5/2001 |
| WO | WO 88/04768 | 6/1988 |
| WO | WO 90/00866 | 2/1990 |
| WO | WO 93/11681 | 6/1993 |
| WO | WO 94/05177 | 3/1994 |
| WO | WO-95/26652 | 10/1995 |
| WO | WO-00/21399 | 4/2000 |
| WO | WO-00/33031 | 6/2000 |
| WO | WO 01/80678 | 11/2001 |
| WO | WO 02/34079 | 5/2002 |
| WO | WO-2007/130287 | 11/2007 |

OTHER PUBLICATIONS

Opposition of Therm-IC-Products GmbH as filed on Jul. 4, 2008, 20 pages.

Response to Opposition Therm-IC Products GmbH as filed Feb. 4, 2009; 23 pages.

* cited by examiner

SHOE HOUSING

CROSS-REFERENCE TO RELATED APPLICATION

This application incorporates by reference, and claims priority to and the benefit of, German patent application Ser. No. 102005014709.7, which was filed on Mar. 31, 2005, the entire disclosure of which is hereby incorporated herein by reference.

TECHNICAL FIELD

The present invention relates to a shoe for receiving a housing of an electronic assembly and to a housing for receiving an electronic assembly.

BACKGROUND

Professional athletes, as well as amateurs, desire in an increasing number of sports to electronically keep track of their athletic performance. For example, electronic speedometers with a plurality of functions are nowadays standard equipment for every ambitious race or mountain biker. Small computers are also used for running to count the number of steps, the speed, and thus the covered distance, and can provide additional information.

Whereas it is comparatively easy to mount a computer to a bicycle, there exists a problem in the case of running. On the one hand, the computer should somehow be connected to the shoe in order to reliably detect the steps of the athlete using, for example, a contact sensor, a shock sensor, or an accelerometer in the shoe sole. On the other hand, the computer must be protected against humidity and mechanical damage. Further, the computer should be easily accessible to view the recorded data and to perform inputs, if desired, or to connect the computer to a PC for further evaluating the measured data.

A similar problem occurs if a runner intends to carry other types of computers, such as, for example, a MP3 player. Although it is generally possible to attach such an electronic assembly to the body using a strap or the like, such an attachment can be uncomfortable and impede movement of the wearer during a high performance activity.

There are many approaches known from the prior art as to how to attach computers to a shoe. For example, U.S. Pat. Nos. 6,536,139 and 6,278,378 and Japanese Publication No. 60 200120, the entire disclosures of which are hereby incorporated herein by reference, disclose arrangements where the computer is attached to the laces or the tongue of the shoe. A modification of this design is disclosed in U.S. Pat. Nos. 4,649,552 and 6,183,425, Japanese Publication No. 60 84689, and PCT Publication No. WO 88/04768, the entire disclosures of which are hereby incorporated herein by reference, where a sensor is integrated into the sole region. The computer, which processes the signals of the sensor to provide useful data, is again arranged in the region of the laces and/or on the instep. U.S. Pat. No. 4,771,394, the entire disclosure of which is hereby incorporated herein by reference, discloses a system where the computer is attached to the heel of the shoe.

All of these arrangements of a computer on a shoe have, however, the disadvantage that the sensitive electronic components of the computer are protected insufficiently against damage. When the runner stumbles or falls, there is a significant risk that the housing of the computer, which is typically made from plastic materials, is subjected to mechanical loads that it can not withstand. Protective coatings, which can be effective, are excluded, since the electronic assembly would reach a size and weight impairing performance of the wearer when the electronic assembly is arranged on the outside of the shoe.

There is, therefore, a need for a shoe that can securely receive an electronic assembly, such as an electronic pedometer, an accelerometer, or a speed sensor, and that overcomes the above discussed disadvantages of the prior art. Furthermore, there is a need for a housing that can securely retain an electronic assembly on a shoe, such that the electronic assembly is permanently protected against damage.

SUMMARY OF THE INVENTION

The problem is solved, in part, by releasably integrating not only a sensor, but a complete electronic assembly, such as a pedometer, an accelerometer, a speed sensor, a MP3 player, or any arbitrary electronic assembly into the shoe sole. Using a cable or a wireless transmission, an additional user interface may be connected to the electronic assembly to allow inputs or the reading of measured data even during operation.

The present invention is based on the realization that the required circuits for electronic assemblies have become smaller and can, therefore, be easily arranged in a recess of the sole of a shoe without significantly affecting the functional properties of the sole (e.g., cushioning and support). At the same time, the electronic assembly is completely enclosed and, therefore, perfectly protected against mechanical impacts. An arrangement in a recess of the sole is also aesthetically pleasing, since the housing of the electronic assembly can not be recognized from the outside.

Since the housing is not permanently integrated into the sole, but only releasably arranged in the recess, it is always possible to replace the housing to, for example, exchange a faulty electronic assembly, exchange the battery, or remove the housing and its electronic assembly from the recess so that it can be connected to a PC or the like for a further evaluation of the data.

The detachable arrangement of the housing also makes the replacement of one electronic assembly for another electronic assembly having a different functionality easy. A unit for detection of a running movement by counting steps or measuring accelerations can thus be exchanged directly against another assembly, for example, a GPS receiver for position determination, a pulse sensor, or other electronic function units. The exchangeability is particularly desirable in the context of an intelligent shoe, where the cushioning properties of the sole can be changed under the control of an electronic control unit. If this control unit is defective, needs to be provided with new firmware, or needs to be exchanged for a more recent model, a mounting arrangement in accordance with the invention can be used in a particularly effective manner. It is also possible for the assembly to be removed in order to exchange, read, expand, etc., the memory of the electronic assembly.

In one aspect, the invention relates to an article of footwear having an upper and a sole unit attached to the upper. The upper forms a cavity for receiving a wearer's foot. The sole unit includes a recess for releasably receiving a housing of an electronic assembly. The recess is at least partially accessible through the cavity of the upper. The upper can be essentially any conventional upper for receiving a wearer's foot, including straps or other structure for surrounding the wearer's foot. In one embodiment, the sole unit includes a tub-like structure for forming the recess.

In various embodiments, the article of footwear includes the housing and the electronic assembly disposed therein. The electronic assembly can be a pedometer, a shock sensor, a global positioning system, a pulse sensor, an accelerometer, a speed sensor, an MP3 player, or combinations thereof. The recess can be arranged in a region of the sole unit corresponding to a wearer's midfoot region. Thus, the housing is arranged in a region of the sole that is subjected to the smallest ground reaction forces and, accordingly, subjected to the smallest deformations.

The sole unit can include an opening or window adapted to permit a wearer to inspect and/or operate the electronic assembly. An additional user interface can also be provided on the shoe. In one embodiment, the recess and housing can be arranged in a midsole of the sole unit, where the sole unit also includes a removable insole for covering the recess when the article is in use. If the housing is arranged in such a recess, it is well protected, since it is surrounded by sole material from all sides. The insole is typically removable and, therefore, does not impair the direct access to the housing of the electronic assembly for, for example, changing the battery. In addition, a shape of the recess can correspond to a shape of the housing for the electronic assembly. The complementary shapes can aide in the retention of the housing within the sole unit by providing a positive fit when the housing is inserted, so that the housing is arranged substantially without play inside the recess of the sole. Vibrations, which after some time could damage an electronic assembly arranged inside the housing, are, therefore, essentially eliminated.

Additionally, the recess can include at least one receptacle engageable by a projection of the housing. The receptacle can be an opening into or through the recess, or an indentation in a wall of the recess. In one embodiment, the receptacle can include additional structure for engaging the projection and/or the receptacle and projection can have complementary shapes. In one embodiment, the recess includes at least two receptacles oriented substantially opposite each other. The recess can include at least one elastic element to secure the housing in the recess. The elastic element can either be formed within the sole unit proximate the recess or be integrated into the recess. The elastic element can be an elastic boundary for circumscribing at least a portion of the housing to rigidly fix the housing inside the recess. As a result, the housing is, in addition to the above-explained positive fit, actively anchored to the recess so that almost any movement of the housing inside the recess is eliminated. Furthermore, the recess can include at least one projection for engaging with a corresponding receptacle in the housing. In one embodiment, the recess includes two projections at each of a front end and a rear end, respectively, in a longitudinal direction of the article of footwear. Each projection is engageable with a corresponding receptacle in the housing. Generally, the receptacles and/or projections of the recess can be formed in the sole unit proximate the recess or disposed in the walls of the recess if, for example, the recess is a separately formed tub-like structure disposed within the sole unit.

The article of footwear can also include a removal strap disposed at least partially within the recess to facilitate removal of the housing from the recess. The removal strap can be arranged within the recess such that a portion of the strap is positioned below the housing when the housing is disposed within the recess and an end of the strap extends over a top edge of the recess. In one embodiment, the removal strap includes an aperture for receiving a projection of the housing, when the housing is disposed in the recess of the article. Further, at least a portion of the recess can be integrated into or formed by at least a portion of a reinforcing element of the sole. The reinforcing element can be a support bar configured to control a rotation of a forefoot portion relative to a rearfoot portion of the sole unit. Such a torsion support or torsion bar is typically made from a substantially incompressible material to achieve the desired support function and is, therefore, particularly suitable for securely receiving the housing for the electronic assembly. Alternatively or additionally, the reinforcing element can be a plate for dispersing impact forces arising on the sole or providing energy return to the wearer's foot during a push-off phase of a step cycle. Examples of reinforcing elements in shoe soles can be found in U.S. Pat. No. 6,199,303 and U.S. patent application Ser. No. 09/561,584, the entire disclosures of which are hereby incorporated by reference herein. Further, tests showed that this arrangement leads to accurate measuring results if an accelerometer is used. The article of footwear can also include an attachment means for securing the article of footwear to a wearer's foot and a mounting cover engageable with the attachment means. The mounting cover can be configured to receive a second housing configured for receiving an electronic assembly. The attachment means for securing the article of footwear onto the wearer's foot includes, for example, laces, hook and loop type fasteners, zippers, snaps, and combinations thereof.

In another aspect, the invention relates to a housing for receiving an electronic assembly. The housing includes a first portion having an exterior surface and a second portion having an exterior surface and releasably coupled to the first portion. The exterior surfaces have a shape configured for engaging a recess formed within a sole of an article of footwear. Such a housing is particularly suited to be used together with a shoe having the above described features and to securely receive an electronic assembly. The housing may be permanently connected to the electronic assembly or the electronic assembly can be releasably arranged inside the housing.

In various embodiments, the housing includes at least one projection disposed on the external surface of at least one of the first portion and the second portion. The projection can extend partially from both portions. The at least one projection can be configured to engage a corresponding receptacle within the recess or formed in the sole unit proximate the recess. In one embodiment, the housing includes at least two projections oriented substantially opposite each other on the housing. The at least two projections can be configured to engage at least two corresponding receptacles within the recess or formed in the sole unit proximate the recess. Furthermore, the projection(s) can be made from an elastic material to facilitate engaging the receptacle of the recess. Additionally, the housing can include at least one receptacle disposed in the first portion or the second portion, or both. The at least one receptacle can be configured to receive a corresponding projection disposed within the recess. In one embodiment, the housing includes two receptacles disposed at each of a front end and a rear end of the housing in a longitudinal direction. Each receptacle can be configured to receive a corresponding projection of the recess. The projection either formed by the sole unit proximate the recess or extending from a sidewall of a separately formed recess, such as the afore-mentioned tub-like structure.

In additional embodiments, the housing includes a cover made of an elastic material. In one embodiment, the cover may encompass substantially the entire housing. Thus, a firm fit in the shoe's recess is on the one hand obtained and, on the other hand, the housing is protected if it is removed from the recess and, for example, falls onto a hard floor. The housing can include a seal arranged between the first portion and the second portion. In one embodiment, the housing includes an opening defined at least partially by at least one of the first portion and the second portion. The opening can be configured to enable access to an interior portion of the housing by a user. The housing can also include a mounting cover engageable with an attachment means for securing the article of footwear to a wearer's foot, the mounting cover configured to releasably receive and at least partially circumscribe the housing. The housing may also be releasably attached in a conventional manner to any arbitrary shoe, if the shoe does not provide a suitable recess in the shoe sole. The use of the housing and the electronic assembly arranged therein does, therefore, not necessarily require the use of a unique pair of shoes. Moreover, the mounting cover makes it possible to use the assembly additionally or alternatively for a display or the like, being arranged on the laces and displaying data measured and/or generated by a further assembly within the shoe.

The mounting cover can include an attachment strap extending below the housing and configured to engage with the attachment means of the article of footwear. In one embodiment, the mounting cover includes at least one mounting arm extending below the housing and below the attachment means of the article of footwear. The mounting arm can include an end region at least partially encompassing a top surface of the housing. In another embodiment, the mounting cover can include at least two mounting arms extending below the housing and below the attachment means of the article of footwear. The mounting arms can include end regions that at least partially encompass a top surface of the housing. In addition, the mounting cover can include a mounting flap. The mounting flap defining an aperture configured for receiving a projection disposed on the housing.

Moreover, the housing can include an electronic assembly disposed therein. The electronic assembly configured for communicating with a user interface located outside of the housing. In one embodiment, the housing defines an aperture configured for passing a cable therethrough. The cable can be configured to provide communication between the electronic assembly and the user interface. Additionally or alternatively, the electronic assembly can communicate with the user interface in a wireless manner.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

In the following, embodiments of the invention are described with reference to an electronic pedometer in a running shoe. The following interprets the term "pedometer" as any electronic assembly detecting in any manner the running movement electronically, e.g., to determine the number of steps done, the acceleration, the speed, or other physical values in connection with the running movement. It is, however, to be understood that the present invention also relates to the arrangement of other kinds of small electronic assemblies in shoes, including, but not limited to a shock sensor, a global positioning system, a pulse sensor, an accelerometer, a speed sensor, and an MP3 player.

Figure 1A:
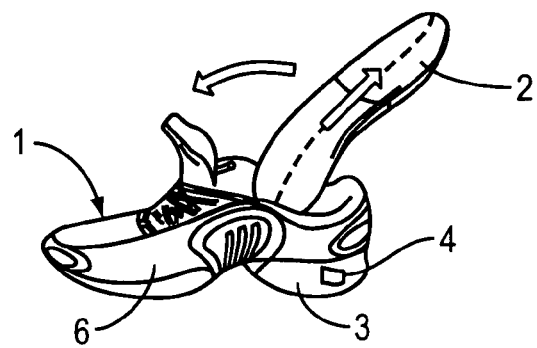
FIGS. 1A and 1B are pictorial representations of the steps required for arranging a housing in a sole unit of a shoe in accordance with one embodiment of the invention.
Figure 1B:
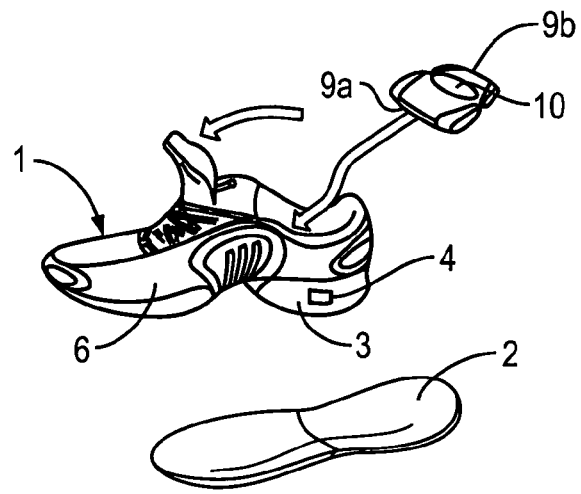

FIGS. 1A and 1B depict an electronic device, such as a pedometer, provided inside a housing 10 having a front end 9a and a rear end 9b arranged in a recess of a sole 3 of a shoe 1 including an upper 6. To this end, a removable insole 2 or a so-called sock liner is at first removed from within the upper 6 (FIG. 1A). Subsequently, the housing 10 is arranged in a recess of the midsole through the upper 6 (FIG. 1B). The recess for receiving the housing 10 may alternatively also be provided in a removable insole 2 or the midsole and the insole 2 together may form a cavity for the housing 10. In general, it is also possible to provide the recess for releasably receiving the housing 10 in an outsole. In another modification of the described embodiment, the electronics of the device can be fully integrated into the removable insole of the running shoe.

Furthermore, the electronic assembly 10 may be operated after it has been arranged in one of the afore-mentioned sole layers. For example, openings 4 can be arranged in the surrounding sole layers or keys can be provided that allow the operation of corresponding input means on the housing 10. It is also possible to manufacture parts of the sole layers surrounding the inserted housing 10 from a transparent material to allow for inspection of a display on the housing 10 or to allow the transmission of a light signal that might, for example, indicate the proper functioning of the electronic assembly. Alternatively or additionally, infrared light can be used to exchange signals with the electronic assembly to, for example, send a command to the electronic assembly or acquire data therefrom. In one embodiment, the housing 10 itself includes a window and/or provisions for the use of operating keys with the electronic assembly, if required, or for observing a display.

Figure 2:
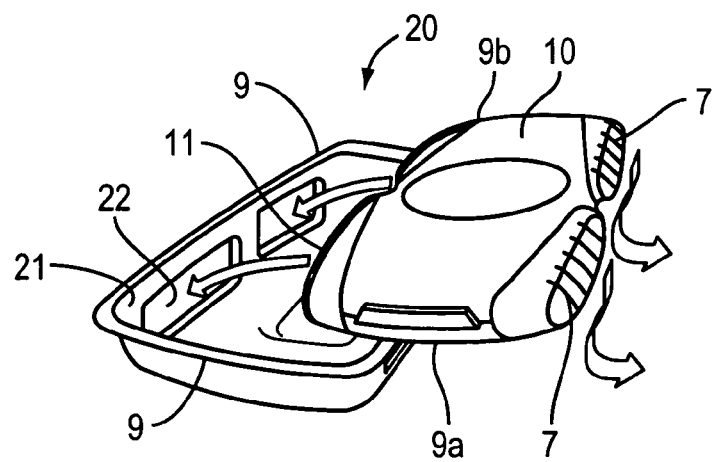
FIG. 2 is a schematic perspective view of how the housing is inserted into a recess of the sole unit in accordance with one embodiment of the invention.

An exemplary illustration of a recess 20 in the midsole is shown in FIG. 2. For the sake of simplicity, the midsole material surrounding the recess 20 is not shown. The recess 20 has substantially the shape of a tub, wherein at least one of its inner dimensions, i.e., its length, width, or depth corresponds substantially to the outer dimensions of the housing 10. In one embodiment, all of the dimensions correspond. The recess 20 may include elastic inserts or edge sections to ensure a firm fit of the housing 10 in the recess 20. When the housing 10 is inserted into the recess 20, as shown in FIG. 2, there is a positive fit so that relative movements inside the recess 20 are substantially excluded. Furthermore, it is desirable for the top surface of the inserted housing 10 to be substantially flat to avoid bulges in the insole 2 and, therefore, such an arrangement of the housing 10 has no significant influence on the wearing comfort of the shoe 1.

In one embodiment, the recess 20 can be formed within the sole or, alternatively, the recess 20 can be a tub-like structure integrated into the sole by, for example, injection molding the sole around the recess 20. The recess 20 can be arranged in the midfoot area of the shoe and, for example, integrated into a device for supporting the arch of the foot, which is typically made from a harder material than the surrounding sole material. In one embodiment, an arrangement of the recess 20 in a support bar (FIG. 9) allows torsional flex of the foot, i.e., rotation of the forefoot relative to the rearfoot. Furthermore, the recess 20 can be located in other regions of the sole, for example the forefoot or heel regions, and more than one recess 20 can be provided. In one embodiment, multiple recesses 20 can be included, where the sizes of the recesses 20 can vary to suit a particular application or type of electronic device.

FIG. 2 discloses one possible manner in which the housing 10 may be attached to the recess 20. Specifically, receptacles 22, such as through openings or indentations, are located in the sidewalls 21 of the recess 20, and projections 11 extending from the housing 10 extend into and/or through the receptacles, thereby, attaching the housing 10 inside the recess 20. As can be seen from FIG. 2, the sidewalls 21 include several receptacles 22 that can be arranged in pairs on opposing sidewalls 21. The sidewalls 21 may be the longitudinal sides and/or the lateral sides of the recess 20.

Figure 3:
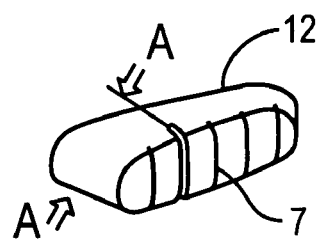
FIG. 3 is a schematic perspective view of a projection of a housing coated by a rubber layer in accordance with one embodiment of the invention.
Figure 4A:
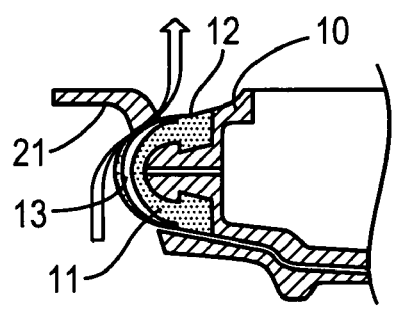
FIG. 4A is a schematic cross-sectional view of the projection of FIG. 3 taken along the line A-A in FIG. 3, when the projection is disposed on the housing of FIG. 2 inserted into a receptacle of the recess.

The arrows in FIG. 2 illustrate how the projections 11 are initially inserted into the corresponding receptacle 22 of a sidewall 21 before the housing 10 is downwardly pressed so that the opposite projections 11 can engage the corresponding receptacles 22 of the opposite sidewall 21. In one embodiment, the sidewalls 21 and/or the projections 11 have a certain elasticity. In one embodiment, the projections 11 have an optional outer rubber coating 12 (FIG. 3) providing the required elasticity. The rubber coating 12 may either be made from a continuous rubber material or it has inner cavities (FIG. 4) filled by air or, if necessary, specific cushioning materials, such as a gel. For an easier handling of the housing 10, the outside of the rubber coating 12 may include one or more profile elements 7. The outer rubber coating 12 is compliant and, thereby, aides in the insertion of the housing 10 within the recess 20. In other words, the projections 11 (or recess 20) may bend or otherwise yield to the force required to insert the housing 10 within the recess 20, but then return to their original shape to hold the housing 10 within the recess 20.

The rubber coating 12 additionally protects the housing 10 and the electronic components of the device arranged therein, when the housing 10 is removed, for example for connecting to a PC, and unintentionally dropped. It is, therefore, also possible to provide the housing 10 with a rubber coating that covers not only the disclosed four projections 11, but also completely covers the housing 10, as explained below in more detail with reference to the alternative embodiment shown in FIG. 11. This is particularly desirable when a mounting cover is used, as described subsequently, such that the housing 10 is arranged on the laces without the protection of the surrounding sole material.

In an embodiment of the invention where the electronic device uses a shock sensor, it is desirable to anchor the housing 10 in the recess 20 without any play. Any acceleration acting on the housing 10 and, thereby, on the device corresponds to an acceleration of the shoe 1 and not to a relative movement between the housing 10 and the shoe 1. This secure fit can be accomplished by, for example, sizing the recess 20 and housing 10 such that there is a slight interference fit therebetween. The elastic nature of at least portions of the recess 20 can allow the edges 9 or sidewalls 21 of the recess 20 to expand to receive the housing 10 and contract to hold the inserted housing 10.

Figure 4B:
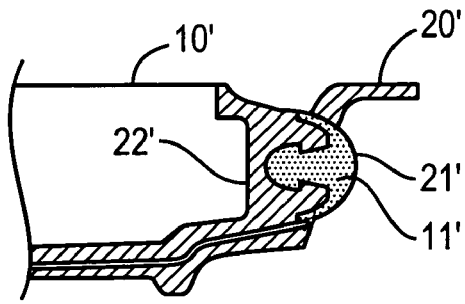
FIG. 4B is an alternative schematic cross-sectional view of the embodiment of FIG. 4A, where the projection is disposed within the recess and received within a receptacle on the housing.

FIG. 4B depicts an alternative arrangement of the projections 11 and the receptacles 22 described hereinabove. As shown in FIG. 4B, the projections 11' are located within the recess 20' and are configured to engage receptacles 22' located on the housing 10'. In the embodiment shown, the projections 11' extend inwardly from the sidewalls 21' of the recess 20'.

Figure 5:
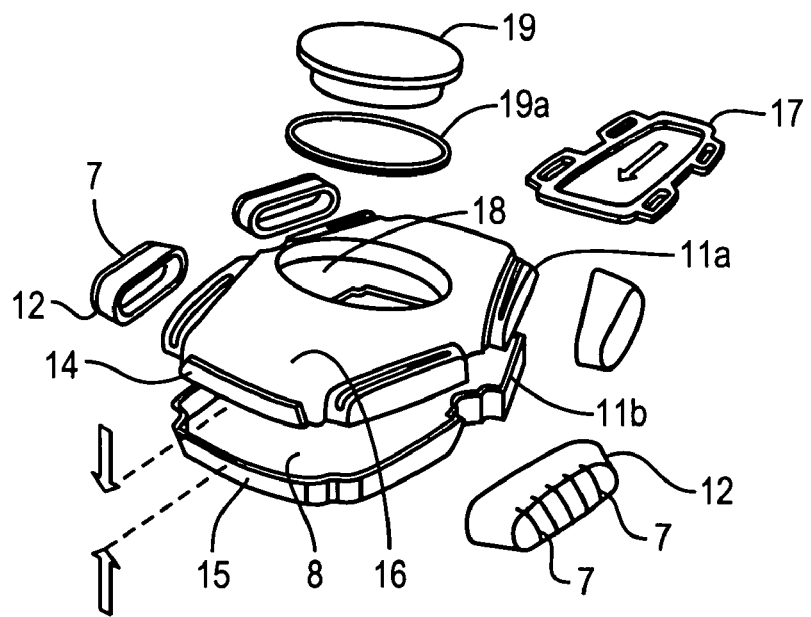
FIG. 5 is an exploded schematic perspective view of the housing of FIG. 2.

FIG. 5 shows an exploded view of one embodiment of a housing 10 in accordance with the invention. As can be seen, the construction includes a first portion, i.e., lower half 15, a second portion i.e., upper half 16, and an intermediate seal 17 disposed therebetween to avoid the penetration of dirt and/or humidity. The seal 17 is desirable when the two portions 15, 16 are releasably interconnected to allow the removal of an electronic assembly arranged in the interior 8 of the housing 10. Alternatively, it is also possible to permanently interconnect the two portions 15, 16 after the initial installation of the electronic assembly by, for example, gluing, fasteners, high-frequency welding, or other techniques.

In the embodiment of FIG. 5, the two portions 15, 16 are interconnected by having the integral rubber coating 12 extending over both the upper half 11a and the lower half 11b of a lateral projection 11 of the housing 10. Additionally or alternatively, latches and/or screws can be used for interconnecting the upper and the lower portion 15, 16 of the housing 10. Furthermore, in one embodiment, the housing 10 can be formed as a single component.

As further shown in FIG. 5, the housing 10 can include an opening 18 on its top side with a cover 19 and a seal 19a, for example an O-ring. As a result, a battery or an accumulator can be easily replaced, without the housing 10 having to be removed from the recess 20. Instead of an opening, the housing 10 could also include a charging socket so that an accumulator arranged in its interior can be charged externally by using a cable.

Figure 6:
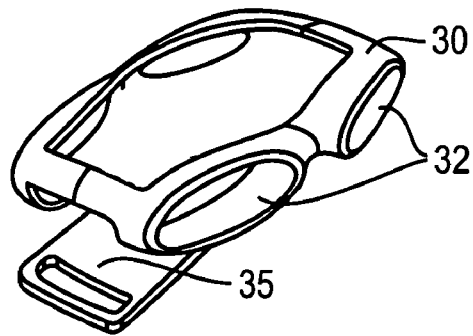
FIG. 6 is a schematic perspective view of a mounting cover for the housing of FIG. 2 in accordance with one embodiment of the invention.
Figure 7:
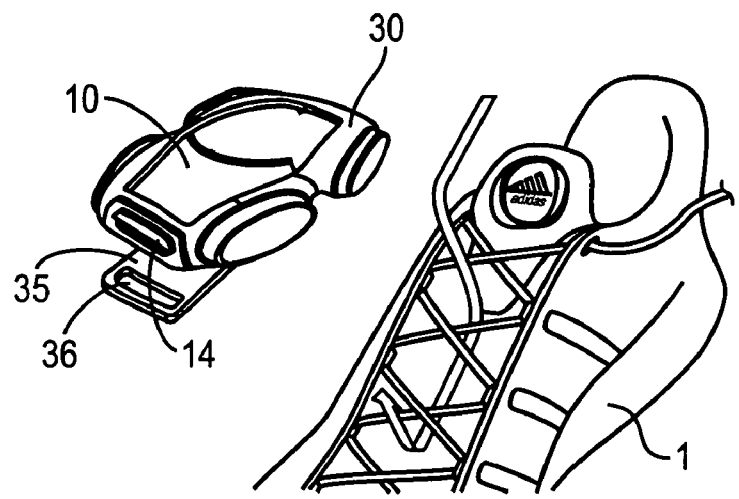
FIGS. 7 and 8 are schematic perspective views showing how the housing of FIG. 2 and the mounting cover of FIG. 6 can be attached to the laces of a shoe in accordance with one embodiment of the invention.
Figure 8:
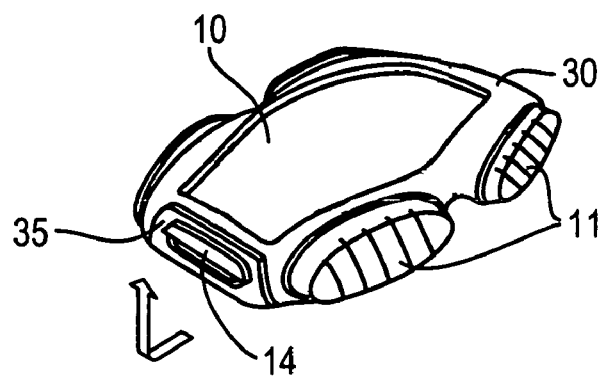

FIGS. 6 to 8 illustrate an embodiment of a mounting cover 30 in accordance with the invention. The mounting cover 30 allows for the attachment of the above-described housing 10 to the fastening means, for example laces, of a common shoe. This arrangement can be used where the shoe does not include the above-described recess 20 or if an additional electronic assembly, for example an MP3 player, is to be attached to the shoe in addition the first electronic assembly, for example a pedometer. Similar to the recess 20, the mounting cover 30 comprises side-walls with receptacles 32 that can be penetrated by the projections 11 of the housing 10. As a result, the housing 10 can reliably, but releasably, be fixed to the mounting cover 30. Also the receptacles 32, either as openings or indentations, can be arranged in opposite pairs. The depicted embodiment has a shape and size corresponding substantially to the external dimensions of the housing 10 and includes four receptacles 32, similar to the above-described embodiment of the recess 20, that are engaged by the four corresponding projections 11 of the housing 10 (FIG. 8).

In one embodiment, the mounting cover 30 may include an attachment strap 35 located on its lower side. The attachment strap 35 provides a removable connection to the laces (FIG. 7) or to other attachment means for securing a shoe to a wearer's foot. The attachment strap 35 is guided below the laces and includes an aperture 36 located on its free end that can be releasably attached to a front end 9a of the housing 10 (FIG. 8). To this end, a suitable projection 14 can be arranged on the front end of the housing 10. Other attachment means are also possible and considered within the scope of the invention, including, for example, a snap-fastener for securely connecting the free end of the attachment strap 35 to the housing 10 and/or the mounting cover 30.

Figure 9:
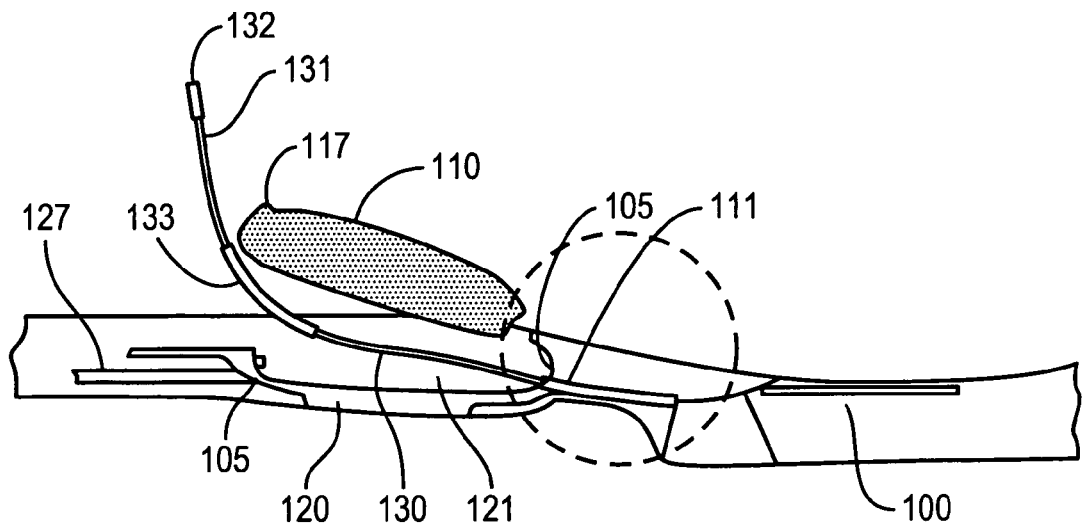
FIG. 9 is a schematic cross-sectional view depicting how the housing may be arranged in a sole unit in accordance with an alternative embodiment of the invention.
Figure 10:
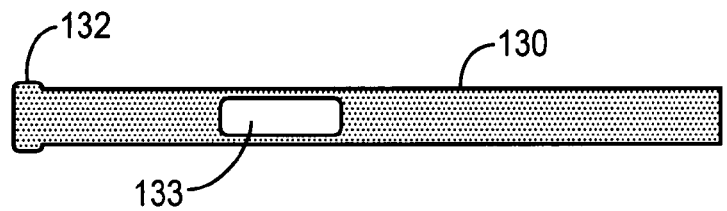
FIG. 10 is a schematic plan view of a removal strap from the embodiment of FIG. 9 for facilitating the removal of the housing from the recess in accordance with one embodiment of the invention.
Figures 11, 12:
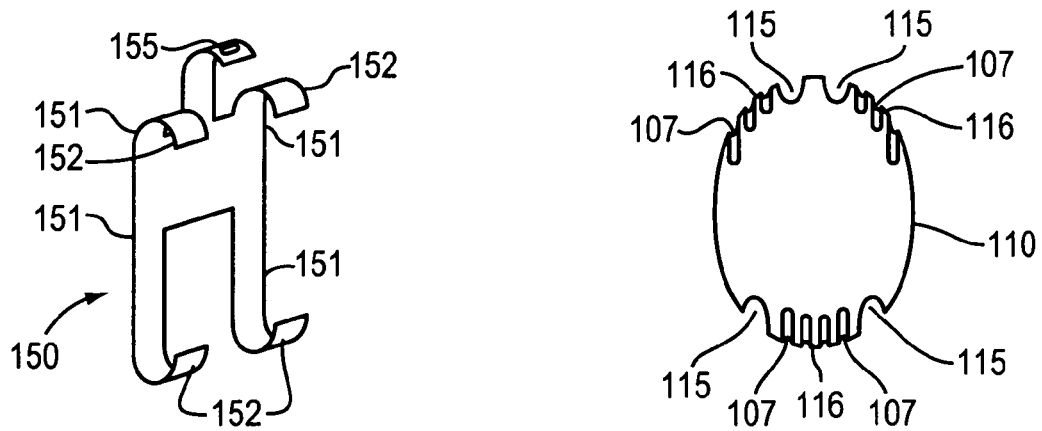
FIG. 11 is a schematic plan view of an alternative embodiment of a housing in accordance with the invention.
FIG. 12 is a schematic perspective view of a mounting cover adapted for use with the housing of FIG. 11.

FIGS. 9, 10, and 11 depict an alternative embodiment of the invention. As described above, an approximately tub-like recess 120 is again arranged in a midfoot region of a shoe sole 100, for example, in a midsole, the inner dimensions of which correspond substantially to the outer dimensions of a corresponding housing 110. As shown in FIG. 11, the housing 110 has an approximately turtle-like shape. In the embodiment shown in FIG. 9, the shoe sole 100 includes an optional torsion bar 127 disposed therein. The recess 120 either passing through or at least partially defined by the torsion bar 127.

In a lateral region (e.g., at the front end of the recess 120) that is marked in FIG. 9 by a dashed circle, there is a slit 111 into which a removal strap 130 can be mounted by, for example, gluing. When the housing 110 is inserted into the recess 120, as shown in FIG. 9, the removal strap 130 lies flat below the housing 110. Only a boundary region 131, optionally including a reinforcement 132 to facilitate gripping, protrudes from the recess 120. Since, however, the boundary region 131 and the reinforcement 132 are preferably arranged below an insole, i.e., a sock liner, the comfort of wearing the shoe is unimpaired.

The removal strap 130 facilitates removal of the housing 110 of the electronic assembly from the shoe sole 100. Despite a firm fit in the recess 120, as obtained by, for example, covering the housing 110 with an elastic layer (e.g., rubber) the housing 110 may be removed from the recess 120 of the sole 100 simply by pulling the removal strap 130. Neither a particular force nor specific tools are required. In one embodiment, the removal strap is substantially flexible to conform to the shape of the housing 110 and recess 120.

FIG. 10 shows one embodiment of the removal strap 130. The removal strap 130 has a substantially elongate shape and includes an optional aperture 133 disposed therein. A projection 117 of the housing 110 (FIG. 11) can pass through the aperture 133 and engage the recess 120 in the mounted position of the housing 110. Thus, the removal strap 130 is correctly aligned to facilitate the later removal of the housing 110 in the manner explained above.

FIG. 11 depicts an embodiment of the housing 110 that includes a plurality of optional indentations 115 that can be arranged in pairs at the front and rear ends of the housing 110. Corresponding projections 105 arranged in the interior 121 of the recess 120 can engage these indentations 115, for example in pairs at the front and rear ends of the recess 120. Thus, the housing 110 is firmly positioned in the recess 120. Alternatively, embodiments of the invention are possible where the housing 110 is only arranged in an approximately correspondingly shaped recess 120 of the shoe sole, without any further measures.

In addition, to improve handling of the housing and the electronic assembly with its sensitive circuits arranged therein, the rubber layer can have regions 116 with groove-like indentations 107 disposed thereon to promote a secure grip. The embodiment of FIG. 11 shows three such regions 116 located, for example, at the front end of the housing 110 besides the indentations 115 and at the rear end of the housing 110 between the two rear indentations, respectively. Measures other than the interaction of the afore-mentioned projections and indentations are possible to ensure a secure mounting of the housing 110 in the recess 120. For example, the housing 110 may be fixed in a certain position by a magnet, or the recess 120 may include a closable cover that additionally fixes the removable housing 110 therein.

An alternative embodiment of a mounting cover 150 that can used with the embodiment of the housing 110 of FIG. 11, is shown in FIG. 12. The mounting cover 150 will only encompass the housing 110 partially. The mounting cover 150 has arms 151 configured to extend beneath the laces, or other attachment means of the shoe, and end in hook-like, upwardly bent end regions 152, thereby forming a receptacle for receiving the housing 110. The housing 110 is clipped into the thus-formed receptacle from the top so that the hook-like end regions 152 encompass the housing at its top surface. Instead of the four arms 151 shown in FIG. 12, other numbers of arms are possible, e.g., three arms or only two arms of wider dimensions, encompassing the housing 110 at the top and bottom end or at the sides. Further, a mounting flap 155 may be included on the mounting cover 150, as shown in FIG. 12, extending over the projection 117 and thus anchoring the housing 110 securely in the mounting cover 150 in addition to the clipping of the housing 110 within the hook-like end regions 152.

Figure 13:
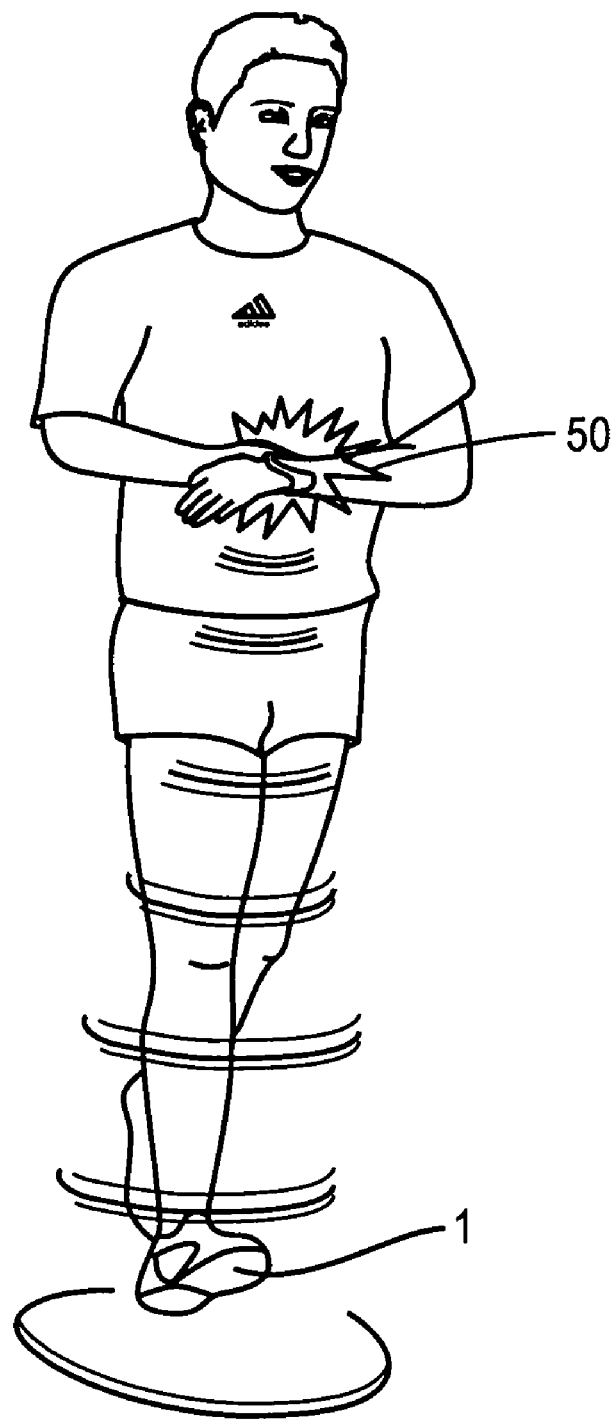
FIG. 13 is a pictorial representation showing how an electronic assembly can communicate in a wireless manner with a user interface provided on a receiving unit attached to a user.

FIG. 13 discloses an optional manner of controlling the electronic assembly arranged inside the sole or on the instep, in addition to or alternatively to the above described input possibilities through the sole. Using a wireless link, the electronic assembly arranged in the housing 10 inside the shoe sole communicates with a receiving unit 50 carried, for example, on the wrist. To this end, a wireless transmission standard such as Bluetooth® or the like may be used. Since the actual electronics are arranged inside the housing in the shoe sole, the receiving unit 50 at the wrist (or at any other position) can be very light-weight, small and, for example, be integrated into a watch or garment. In addition, an arrangement in a strap similar to an electronic assembly for measuring the pulse is also possible.

The wireless transmission between the unit 50 and the electronic assembly inside or at the shoe sole may be bi-directional, so that the electronic assembly can be controlled using the unit 50. Instead of a wireless transmission, a thin cable may be used which is guided through the housing 10 to the outside and connected to a control and/or display unit outside the shoe sole.

Moreover, the electronic assembly may be electrically connected to a plurality of additional sensors that are not arranged in the housing itself, but at other locations in the shoe, for example, in the sole region, in the shoe upper, in the forefoot region, in the rearfoot region, etc. Since not all possible connections to the electronic assembly are required for every shoe, it is also possible that only a portion of a plurality of provided electrical connections are actually connected. This is in particular sensible if an offerer distributes an electronic assembly that is able to detect a large number of different parameters (speed, acceleration, GPS position, deformation of the shoe, pulse rate, etc.) during running, which are provided by a complex and thus expensive shoe with the entirety of all possible sensors. Due to its modular character, the device can, however, also be used with a simpler and less expensive shoe in which only a portion of the sensors is actually provided.

The various components, for example the tub-like structure, can be manufactured as a single plastic part by injection molding or extrusion. Both methods lead to very low manufacturing costs, a low weight, easy adaptation to different sizes, for example adult versus children shoes, by using correspondingly adapted molds for injection molding. In some embodiments, the components can be manufactured by multi-component injection molding more than one plastic material. For example, a harder plastic material can be used for the housing 10 and a particularly soft and elastic plastic material can be used for the projections 11. The multi-component injection molding may be performed simultaneously using one or more nozzles or sequentially. Alternatively, the plastic material can be injected around separately pre-manufactured components.

Suitable plastic materials include: thermoplastic polyurethanes (TPU); polypropylene (PP); ethylene vinyl acetate (EVA); thermoplastic polyether block amides, such as the Pebax® brand sold by Elf Atochem; thermoplastic polyester elastomers, such as the Hytrel® brand sold by DuPont; thermoplastic elastomers, such as the Santoprene® brand sold by Advanced Elastomer Systems, L.P.; thermoplastic olefin; nylons, such as nylon 12, which may include 10 to 30 percent or more glass fiber reinforcement; silicones; polyethylenes; acetal; and equivalent materials. Reinforcement, if used, may be by inclusion of glass or carbon graphite fibers or para-aramid fibers, such as the Kevlar® brand sold by DuPont, or other similar method. Also, the polymeric materials may be used in combination with other materials, for example natural or synthetic rubber. Other suitable materials will be apparent to those skilled in the art.

Moreover, the material selection, as well as the size and shape of the housing 10 and recess 20 can vary to suit a particular application and can easily be optimized using a finite-element-analysis. For example, the housing 10 can have essentially any shape, such as polygonal, arcuate, or combinations thereof, and be sized based, at least in part, on the type of electronic assembly housed therein and the specific location the housing will be mounted or inserted into.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

What is claimed is:

1. An article of footwear comprising:
   an upper forming a cavity for receiving a wearer's foot;
   a sole unit attached to the upper and forming a recess;
   at least one receptacle disposed within the recess, wherein the at least one receptacle is at least partially accessible through the cavity of the upper; and
   a housing for receiving an electronic assembly, wherein the housing includes at least one projection configured to engage the at least one receptacle, and the at least one receptacle is configured to releasably receive the housing.

2. The article of footwear of claim 1, wherein the at least one receptacle comprises a tub-like structure.

3. The article of footwear of claim 1 further comprising an electronic assembly disposed in the housing, wherein the electronic assembly is at least one of a pedometer, a shock sensor, a global positioning system, a pulse sensor, an accelerometer, a speed sensor, and an MP3 player.

4. The article of footwear of claim 1, wherein the recess is arranged in a region of the sole unit corresponding to a wearer's midfoot region.

5. The article of footwear of claim 1, wherein the sole unit forms an opening adapted to permit a wearer to at least one of inspect and operate an electronic assembly disposed in the housing.

6. The article of footwear of claim 1, wherein the recess is arranged in a midsole of the sole unit, and the sole unit further comprises a removable insole for covering the recess and the at least one receptacle when the article is in use.

7. The article of footwear of claim 1, wherein a shape of the at least one receptacle corresponds to a shape of the housing.

8. The article of footwear of claim 1, wherein the at least one receptacle comprises at least two openings oriented substantially opposite each other.

9. The article of footwear of claim 1, wherein the at least one receptacle comprises at least one elastic element to secure the housing in the at least one receptacle.

10. The article of claim 9, wherein the elastic element comprises an elastic boundary for circumscribing at least a portion of the housing.

11. The article of footwear of claim 1, wherein the at least one receptacle comprises at least one projection engageable with a corresponding indentation in the housing.

12. The article of footwear of claim 1, wherein the at least one receptacle comprises two projections at each of a front end and a rear end, respectively, in a longitudinal direction of the article, wherein each projection is engageable with a corresponding indentation in the housing.

13. The article of footwear of claim 1 further comprising a removal strap disposed at least partially within the at least one receptacle to facilitate removal of the housing from the at least one receptacle.

14. The article of footwear of claim 13, wherein the removal strap is arranged within the at least one receptacle such that a portion of the strap is positioned below the housing when the housing is disposed within the at least one receptacle and an end of the strap extends over a top edge of the at least one receptacle.

15. The article of footwear of claim 13, wherein the removal strap comprises an aperture for receiving a projection of the housing when the housing is disposed in the at least one receptacle of the article.

16. The article of footwear of claim 1, wherein at least a portion of the at least one receptacle is integrated into a reinforcing element disposed within the sole unit.

17. The article of footwear of claim 1, further comprising:
   an attachment means for securing the article of footwear to a wearer's foot; and
   a mounting cover engageable with the attachment means, wherein the mounting cover is configured to receive a second housing configured for receiving an electronic assembly.

18. The article of footwear of claim 1, wherein the sole unit forms a plurality of recesses, and the at least one receptacle is disposed within at least one of the plurality of recesses.

19. The article of footwear of claim 1, wherein the at least one receptacle comprises at least two indentations oriented substantially opposite each other.

20. An article of footwear comprising:
    an upper forming a cavity for receiving a wearer's foot;
    a sole unit attached to the upper and forming a recess;
    at least one tub-like receptacle disposed within the recess, wherein the at least one receptacle is at least partially accessible through the cavity of the upper; and
    a housing for receiving an electronic assembly, wherein the housing includes at least one projection configured to engage the at least one receptacle, and the at least one receptacle is configured to releasably receive the housing.

21. An article of footwear comprising:
    an upper forming a foot-receiving cavity;
    a sole unit attached to the upper, wherein the sole unit includes an outsole and a midsole located between the outsole and the foot-receiving cavity, wherein the midsole has an opening or recess defined therein;
    a receptacle provided in the opening or recess, wherein the receptacle is at least partially accessible through the foot-receiving cavity;
    a housing comprising an electronic assembly, wherein the housing is removably mounted in the receptacle; and
    a system for securing the housing to the receptacle, wherein the system includes a projection that extends into an indentation defined in the housing.

\* \* \* \* \*

UNITED STATES PATENT AND TRADEMARK OFFICE
CERTIFICATE OF CORRECTION

PATENT NO. : 7,596,891 B2
APPLICATION NO. : 11/394132
DATED : October 6, 2009
INVENTOR(S) : Carnes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this

Twenty-eighth Day of September, 2010

David J. Kappos
*Director of the United States Patent and Trademark Office*